United States Patent
Stürmer et al.

(10) Patent No.: US 8,012,725 B2
(45) Date of Patent: Sep. 6, 2011

(54) METHOD FOR THE PRODUCTION OF OPTICALLY-ACTIVE ALCOHOLS

(75) Inventors: Rainer Stürmer, Rödersheim-Gronau (DE); Bernhard Hauer, Fußgöheim (DE); Dejana Drew, Mannheim (DE); Michael Breuer, Darmstadt (DE); Hartwig Schröder, Nußloch (DE)

(73) Assignee: BASF SE, Ludwigshafen (DE)

( * ) Notice: Subject to any disclaimer, the term of this patent is extended or adjusted under 35 U.S.C. 154(b) by 709 days.

(21) Appl. No.: 11/667,721

(22) PCT Filed: Nov. 15, 2005

(86) PCT No.: PCT/EP2005/012234
§ 371 (c)(1),
(2), (4) Date: May 14, 2007

(87) PCT Pub. No.: WO2006/053713
PCT Pub. Date: May 26, 2006

(65) Prior Publication Data
US 2008/0009046 A1    Jan. 10, 2008

(30) Foreign Application Priority Data
Nov. 17, 2004 (DE) .......................... 10 2004 055 508

(51) Int. Cl.
| C12P 7/16 | (2006.01) |
| C12P 7/02 | (2006.01) |
| C12P 7/04 | (2006.01) |
| C12Q 1/26 | (2006.01) |
| C12Q 1/32 | (2006.01) |
| C12N 1/00 | (2006.01) |
| C12N 1/20 | (2006.01) |
| C12N 9/02 | (2006.01) |
| C07H 21/04 | (2006.01) |

(52) U.S. Cl. ............ 435/160; 435/25; 435/26; 435/155; 435/157; 435/243; 435/252.33; 435/189; 536/23.2

(58) Field of Classification Search .................. None
See application file for complete search history.

(56) References Cited

U.S. PATENT DOCUMENTS
5,763,236 A    6/1998 Kojima et al.
2007/0265477 A1*    11/2007 Gupta et al. .................. 568/913

FOREIGN PATENT DOCUMENTS
| CA | 2004-2529583 A1 | * 12/2005 |
| WO | WO-01/70955 | 9/2001 |
| WO | WO2004-111083 A2 | * 12/2004 |

OTHER PUBLICATIONS

Whisstock et al. Quaterly Reviews of Biophysics, 2003, "Prediction of protein function from protein sequence and structure", 36(3): 307-340.*
Rabus et al. The genome sequence of an anaerobic aromatic-degrading denitrifying bacterium, strain EbN1, Arch Microbiol. Jan. 2005;183(1):27-36. Epub Nov. 13, 2004.*
Clark et al. Can immobilization be exploited to modify enzyme activity? Trends Biotechnol. Nov. 1994;12(11):439-43, Review.*
Velonia, K. et al., "Stereospecificity of Hydrogen Transfer by the NAD+-linked Alcohol Dehydrogenase from the Antarctic Psychrophile *Moraxella* sp. TAE123.", Bioorganic & Medicinal Chemistry Letters, 1999, vol. 9, pp. 65-68.
Matsuda, T. et al., "Asymmetric Reduction of Simple Aliphatic Ketones with Dried Cells of *Geotrichum candidum*", Tetrahedron: Asymmetry, 2002, vol. 13, pp. 971-974.
Bradshaw, C. W. et al., "A *Pseudomonas* sp. Alcohol Dehydrogenase with Broad Substrate Specificity and Unusual Stereospecificity for Organic Synthesis", J. Org. Chem., 1992, vol. 57, pp. 1526-1532.
Keinan, E. et al., "Thermostable Enzymes in Organic Synthesis. 2. Asymmetric Reduction of Ketones with Alcohol Dehydrogenase from *Thermoanaerobium brockii*", J. Am. Chem. Soc., 1986, vol. 108, pp. 162-169.
"*E. coli* Cellular Proliferation Protein #150.", Genseq Database Accession No. AAU34569, Feb. 14, 2002.
"Alcohol Dehydrogenase, Propanol-Preferring.", Uniprot Database Accession No. P39451, Feb. 1, 1997.
Blattner, F. R. et al., "The Complete Genome Sequence of *Escherichia coli* K-12", Science, 1997, vol. 277, pp. 1453-1462.
Otsuka, K. et al., "Regeneration of NADH and Hydrogenation of Ketones to Alcohols with the Combination of Hydrogenase and Alcohol Dehydrogenase", Chemistry Letters, 1987, pp. 2089-2090.
Oritani, H. et al., "Purification and Characterization of Pig Lung Carbonyl Reductase", Archives of Biochemistry and Biophysics, 1992, vol. 292, No. 2, pp. 539-547.
Nakamura, K. et al., "Recent Developments in Asymmetric Reduction of Ketones with Biocatalysts", Tetrahedron: Asymmetry, 2003, vol. 14, pp. 2659-2681.

* cited by examiner

*Primary Examiner* — Anand Desai
*Assistant Examiner* — Iqbal H Chowdhury
(74) *Attorney, Agent, or Firm* — Connolly Bove Lodge & Hutz, LLP (57) ABSTRACT

The present invention relates to enzymic processes for preparing S-butan-2-ol; and to enzymes for carrying out said processes; to nucleic acid sequences coding for said enzymes, to expression cassettes, vectors and recombinant hosts containing said nucleic acid sequences.

7 Claims, 1 Drawing Sheet

Figure 1 Reduction of butan-2-one to S-butan-2-ol, catalyzed by *Escherichia coli* propanol dehydrogenase.

SEQUENCE LISTING

<160> NUMBER OF SEQ ID NOS: 4

<210> SEQ ID NO 1
<211> LENGTH: 1041
<212> TYPE: DNA
<213> ORGANISM: Escherichia coli
<220> FEATURE:
<221> NAME/KEY: CDS
<222> LOCATION: (1)..(1041)

<400> SEQUENCE: 1

```
atg cag aac atc atc cga aaa gga gga act atg aag gct gca gtt gtt     48
Met Gln Asn Ile Ile Arg Lys Gly Gly Thr Met Lys Ala Ala Val Val
1               5                   10                  15 acg aag gat cat cat gtt gac gtt acg tat aaa aca ctg cgc tca ctg     96
Thr Lys Asp His His Val Asp Val Thr Tyr Lys Thr Leu Arg Ser Leu
            20                  25                  30
```

```
aaa cat ggc gaa gcc ctg ctg aaa atg gag tgt tgt ggt gta tgt cat        144
Lys His Gly Glu Ala Leu Leu Lys Met Glu Cys Cys Gly Val Cys His
         35                  40                  45 acc gat ctt cat gtt aag aat ggc gat ttt ggt gac aaa acc ggc gta        192
Thr Asp Leu His Val Lys Asn Gly Asp Phe Gly Asp Lys Thr Gly Val
 50                  55                  60 att ctg ggc cat gaa ggc atc ggt gtg gtg gca gaa gtg ggt cca ggt        240
Ile Leu Gly His Glu Gly Ile Gly Val Val Ala Glu Val Gly Pro Gly
65                  70                  75                  80 gtc acc tca tta aaa cca ggc gat cgt gcc agc gtg gcg tgg ttc tac        288
Val Thr Ser Leu Lys Pro Gly Asp Arg Ala Ser Val Ala Trp Phe Tyr
                 85                  90                  95 gaa gga tgc ggt cat tgc gaa tac tgt aac agt ggt aac gaa acg ctc        336
Glu Gly Cys Gly His Cys Glu Tyr Cys Asn Ser Gly Asn Glu Thr Leu
            100                 105                 110 tgc cgt tca gtt aaa aat gcc gga tac agc gtt gat ggc ggg atg gcg        384
Cys Arg Ser Val Lys Asn Ala Gly Tyr Ser Val Asp Gly Gly Met Ala
        115                 120                 125 gaa gag tgc atc gtg gtc gcc gat tac gcg gta aaa gtg cca gat ggt        432
Glu Glu Cys Ile Val Val Ala Asp Tyr Ala Val Lys Val Pro Asp Gly
130                 135                 140 ctg gac tcg gcg gcg gcc agc agc att acc tgt gcg gga gtc acc acc        480
Leu Asp Ser Ala Ala Ala Ser Ser Ile Thr Cys Ala Gly Val Thr Thr
145                 150                 155                 160 tac aaa gcc gtt aag ctg tca aaa att cgt cca ggg cag tgg att gct        528
Tyr Lys Ala Val Lys Leu Ser Lys Ile Arg Pro Gly Gln Trp Ile Ala
                165                 170                 175 atc tac ggt ctt ggc ggt ctg ggt aac ctc gcc ctg caa tac gcg aag        576
Ile Tyr Gly Leu Gly Gly Leu Gly Asn Leu Ala Leu Gln Tyr Ala Lys
            180                 185                 190 aat gtc ttt aac gcc aaa gtg atc gcc att gat gtc aat gat gag cag        624
Asn Val Phe Asn Ala Lys Val Ile Ala Ile Asp Val Asn Asp Glu Gln
        195                 200                 205 tta aaa ctg gca acc gaa atg ggc gca gat tta gcg att aac tca cac        672
Leu Lys Leu Ala Thr Glu Met Gly Ala Asp Leu Ala Ile Asn Ser His
210                 215                 220 acc gaa gac gcc gcc aaa att gtg cag gag aaa act ggt ggc gct cac        720
Thr Glu Asp Ala Ala Lys Ile Val Gln Glu Lys Thr Gly Gly Ala His
225                 230                 235                 240 gct gcg gtg gta aca gcg gta gct aaa gct gcg ttt aac tcg gca gtt        768
Ala Ala Val Val Thr Ala Val Ala Lys Ala Ala Phe Asn Ser Ala Val
                245                 250                 255 gat gct gtc cgt gca ggc ggt cgt gtt gtg gct gtc ggt cta ccg ccg        816
Asp Ala Val Arg Ala Gly Gly Arg Val Val Ala Val Gly Leu Pro Pro
            260                 265                 270 gag tct atg agc ctg gat atc cca cgt ctt gtg ctg gat ggt att gaa        864
Glu Ser Met Ser Leu Asp Ile Pro Arg Leu Val Leu Asp Gly Ile Glu
        275                 280                 285 gtg gtc ggt tcg ctg gtc ggc acg cgc cag gat tta act gaa gcc ttc        912
Val Val Gly Ser Leu Val Gly Thr Arg Gln Asp Leu Thr Glu Ala Phe
290                 295                 300 cag ttt gcc gcc gaa ggt aaa gtg gtg ccg aaa gtc gcc ctg cgt ccg        960
Gln Phe Ala Ala Glu Gly Lys Val Val Pro Lys Val Ala Leu Arg Pro
305                 310                 315                 320 tta gcg gac atc aac acc atc ttt act gag atg gaa gaa ggc aaa atc       1008
Leu Ala Asp Ile Asn Thr Ile Phe Thr Glu Met Glu Glu Gly Lys Ile
                325                 330                 335 cgt ggc cgc atg gtg att gat ttc cgt cac taa                           1041
Arg Gly Arg Met Val Ile Asp Phe Arg His
            340                 345
```

<210> SEQ ID NO 2
<211> LENGTH: 346
<212> TYPE: PRT
<213> ORGANISM: Escherichia coli

<400> SEQUENCE: 2

Met Gln Asn Ile Ile Arg Lys Gly Gly Thr Met Lys Ala Ala Val Val
1               5                   10                  15

Thr Lys Asp His His Val Asp Val Thr Tyr Lys Thr Leu Arg Ser Leu
            20                  25                  30

Lys His Gly Glu Ala Leu Leu Lys Met Glu Cys Cys Gly Val Cys His
        35                  40                  45

Thr Asp Leu His Val Lys Asn Gly Asp Phe Gly Asp Lys Thr Gly Val
50                  55                  60

Ile Leu Gly His Glu Gly Ile Gly Val Val Ala Glu Val Gly Pro Gly
65                  70                  75                  80

Val Thr Ser Leu Lys Pro Gly Asp Arg Ala Ser Val Ala Trp Phe Tyr
                85                  90                  95

Glu Gly Cys Gly His Cys Glu Tyr Cys Asn Ser Gly Asn Glu Thr Leu
            100                 105                 110

Cys Arg Ser Val Lys Asn Ala Gly Tyr Ser Val Asp Gly Gly Met Ala
        115                 120                 125

Glu Glu Cys Ile Val Val Ala Asp Tyr Ala Val Lys Val Pro Asp Gly
130                 135                 140

Leu Asp Ser Ala Ala Ala Ser Ser Ile Thr Cys Ala Gly Val Thr Thr
145                 150                 155                 160

Tyr Lys Ala Val Lys Leu Ser Lys Ile Arg Pro Gly Gln Trp Ile Ala
                165                 170                 175

Ile Tyr Gly Leu Gly Gly Leu Gly Asn Leu Ala Leu Gln Tyr Ala Lys
            180                 185                 190

Asn Val Phe Asn Ala Lys Val Ile Ala Ile Asp Val Asn Asp Glu Gln
        195                 200                 205

Leu Lys Leu Ala Thr Glu Met Gly Ala Asp Leu Ala Ile Asn Ser His
210                 215                 220

Thr Glu Asp Ala Ala Lys Ile Val Gln Glu Lys Thr Gly Gly Ala His
225                 230                 235                 240

Ala Ala Val Val Thr Ala Val Ala Lys Ala Ala Phe Asn Ser Ala Val
                245                 250                 255

Asp Ala Val Arg Ala Gly Gly Arg Val Ala Val Gly Leu Pro Pro
            260                 265                 270

Glu Ser Met Ser Leu Asp Ile Pro Arg Leu Val Leu Asp Gly Ile Glu
        275                 280                 285

Val Val Gly Ser Leu Val Gly Thr Arg Gln Asp Leu Thr Glu Ala Phe
290                 295                 300

Gln Phe Ala Ala Glu Gly Lys Val Val Pro Lys Val Ala Leu Arg Pro
305                 310                 315                 320

Leu Ala Asp Ile Asn Thr Ile Phe Thr Glu Met Glu Glu Gly Lys Ile
                325                 330                 335

Arg Gly Arg Met Val Ile Asp Phe Arg His
            340                 345

<210> SEQ ID NO 3
<211> LENGTH: 32
<212> TYPE: DNA
<213> ORGANISM: Artificial sequence

```
<220> FEATURE:
<223> OTHER INFORMATION: Oligonucleotide

<400> SEQUENCE: 3
gggaattcat atgcagaaca tcatccgaaa ag                    32

<210> SEQ ID NO 4
<211> LENGTH: 26
<212> TYPE: DNA
<213> ORGANISM: Artificial sequence
<220> FEATURE:
<223> OTHER INFORMATION: Oligonucleotide

<400> SEQUENCE: 4
cccaagctta gtgacggaaa tcaatc                           26
```

METHOD FOR THE PRODUCTION OF OPTICALLY-ACTIVE ALCOHOLS

RELATED APPLICATIONS

This application is a national stage application (under 35 U.S.C. 371) of PCT/EP2005/012234 filed Nov. 15, 2005, which claims benefit of German application 10 2004 055 508.7 filed Nov. 17, 2004.

DESCRIPTION

The present invention relates to a process for preparing (S)-butan-2-ol by reducing butan-2-one in the presence of an alcohol dehydrogenase.

PRIOR ART

The reduction of butan-2-one to butan-2-ol with various biocatalysts has been described [*J. Org. Chem.* (1992) 57:1526, *Chemistry Letters* (1987) 2089, *Arch. Biochem Biophys.* (1992) 292:539].

However, these studies do not report any enantioselectivities. Furthermore, the preparation of R-butan-2-ol has been published [*J. Am. Chem. Soc.* (1986) 108:162]. In this case, however, enantioselectivities of only 48% ee have been obtained.

The biocatalytic synthesis of S-butan-2-ol has been demonstrated by Nakamura et al. [*Tetrahedron: Asymmetry* (2003) 14:2659, *Tetrahedron: Asymmetry* (2002) 13:971] with enantioselectivities of 94% ee having been achieved. In these studies, dried *Geotrichum candidum* cells are used. The enzyme which catalyzes the reaction stated above has not been described in detail, however.

OBJECT OF THE INVENTION

It was the object to provide a process for preparing (S)-butan-2-ol by enantioselective reduction of butan-2-one, which process delivers a high chemical yield of (S)-butan-2-ol with maximum enantiomeric purity.

DESCRIPTION OF THE INVENTION

The present invention relates to a process for preparing (S)-butan-2-ol by reducing butan-2-one in the presence of an alcohol dehydrogenase
(i) having the polypeptide sequence SEQ ID NO:2, or
(ii) having a polypeptide sequence which is at least 80% identical to the sequence of SEQ ID NO:2.

Alcohol dehydrogenases (abbreviated as ADH hereinbelow) which are suitable for the process of the invention are those ADH which are capable of oxidizing 2-propanol in an NAD$^+$-dependent reaction to give 2-propanone.

Furthermore, the ADH suitable for the process of the invention possess a polypeptide sequence according to SEQ ID NO:2 or a polypeptide sequence which is at least 80%, preferably at least 90%, particularly preferably at least 95% and in particular at least 97%, 98% or 99%, identical to the sequence of SEQ ID NO:2.

A polypeptide with SEQ ID NO:2 is the propanol dehydrogenase obtainable from *Escherichia coli* [Swissprot: locus ADHP_ECOLI, accession P39451; GenBank ID 48994873 region: complement (1550852 to 1551892; *[Science]* (1997) 277:1453]. The isolation of this enzyme is described in the experimental section.

Further suitable ADH are those whose polypeptide sequence has one of the above-mentioned sequence identities with SEQ ID NO:2.

For the purposes described herein, the sequence identity is to be determined by the "GAP" computer program of the Genetics Computer Group (GCG) of the University of Wisconsin, it being intended to employ Version 10.3, using the standard parameters recommended by GCG.

Starting from SEQ ID NO:2, such ADH may be obtained by specific or randomized mutagenesis processes known to the skilled worker. Alternatively, however, it is also possible to screen microorganisms, preferably those of the genera *Alishewanella, Alterococcus, Aquamonas, Aranicola, Arsenophonus, Azotivirga, Brenneria, Buchnera* (aphid P-endosymbionts), *Budvicia, Buttiauxella, Candidatus Phlomobacter, Cedecea, Citrobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia* and *Yokenella*, for ADH which catalyze the corresponding oxidation of 2-propanol to give 2-propanone and whose amino acid sequence already has the required sequence identity to SEQ ID NO:2 or is obtained via mutagenesis processes.

The ADH may be used in a purified or partially purified form or else in the form of the microorganism itself. Processes for recovering and purifying dehydrogenases from microorganisms are sufficiently known to the skilled worker, for example from K. Nakamura & T. Matsuda, "Reduction of Ketones" in K. Drauz and H. Waldmann, Enzyme Catalysis in Organic Synthesis 2002, Vol. III, 991-1032, Wiley-VCH, Weinheim, Germany. Recombinant processes for generating dehydrogenases are likewise known, for example from W. Hummel, K. Abokitse, K. Drauz, C. Rollmann and H. Gröger, Adv. Synth. Catal. 2003, 345, Nos. 1+2, pp. 153-159.

The enantioselective reduction with ADH is preferably carried out in the presence of a suitable cofactor (also referred to as cosubstrate). Cofactors commonly used for reducing the ketone are NADH and/or NADPH. In addition, it is possible to employ ADH as cellular systems which inherently contain cofactor or to add alternative redox mediators (A. Schmidt, F. Hollmann and B. Bühler "Oxidation of Alcohols" in K. Drauz and H. Waldmann, Enzyme Catalysis in Organic Synthesis 2002, Vol. III, 991-1032, Wiley-VCH, Weinheim).

Preference is moreover given to carrying out the enantioselective reduction with ADH in the presence of a suitable reducing agent which regenerates the cofactor oxidized during the reduction. Examples of suitable reducing agents are sugars, in particular hexoses, such as glucose, mannose, fructose, and/or oxidizable alcohols, in particular ethanol, propanol or isopropanol, and also formate, phosphite or molecular hydrogen. In order to oxidize the reducing agent and, connected therewith, to regenerate the coenzyme, a second dehydrogenase may be added, such as, for example, glucose dehydrogenase, if the reducing agent used is glucose, or formate dehydrogenase, if the reducing agent used is formate. Said second dehydrogenase may be used as free or immobilized enzyme or in the form of free or immobilized cells. Its preparation may be carried out both separately and by way of coexpression in a (recombinant) dehydrogenase strain.

A preferred embodiment of the claimed process is to regenerate the cofactors by an enzymic system in which a second dehydrogenase, particularly preferably a glucose dehydrogenase, is used.

The invention further relates to the use of ADH for preparing (R)-butan-2-ol. In this embodiment of the process, racemic butan-2-ol is reacted with ADH, with (S)-butan-2-ol being oxidized selectively to give butan-2-one, while (R)-butan-2-ol remains unchanged. Subsequently, the mixture obtained of butan-2-one and (R)-butan-2-ol can be fractionated by customary processes, for example by distillation, and thus (R)-butan-2-ol can be isolated in a pure form.

The preferred cofactors used in this embodiment are $NAD^+$ and $NADP^+$ which may be regenerated again with appropriate cosubstrates (oxidizing agents). The preferred cosubstrate which may be used here is acetone which, together with the ADH already present and/or an additionally employed dehydrogenase, regenerates the cofactor and is reduced to isopropanol in the process.

"Enantioselectivity" means for the purposes of the present invention that the enantiomer excess, ee (in %), of the S-enantiomer, which is calculated in the known manner according to:

$$ee\ (\%) = S\text{-enantiomer} - R\text{-enantiomer}/(S\text{-enantiomer} - R\text{-enantiomer}) \times 100,$$

is at least 80%, preferably at least 90%, in particular at least 95% and especially at least 97%.

The ADH used according to the invention may be employed in a free or immobilized form. An immobilized enzyme means an enzyme which is fixed to an inert support. Suitable support materials and the enzymes immobilized thereon are disclosed in EP-A-1149849, EP-A-1 069 183 and DE-A 100193773 and in the references cited therein. On this matter, reference is made to the disclosure of these publications in their entirety. Examples of suitable support materials are clays, clay minerals such as kaolinite, diatomaceous earth, perlite, silicon dioxide, aluminum oxide, sodium carbonate, calcium carbonate, cellulose powder, anion exchanger materials, synthetic polymers such as polystyrene, acrylic resins, phenol-formaldehyde resins, polyurethanes and polyolefins such as polyethylene and polypropylene. The support materials are usually employed in a finely divided, particulate form for preparing the supported enzymes, with preference being given to porous forms. The particle size of the support material is usually no more than 5 mm, in particular no more than 2 mm (sieve grade). Analogously, when using the dehydrogenase as whole cell catalyst, a free or immobilized form may be chosen. Examples of support materials are calcium alginate and carrageenan. Enzymes as well as cells may also be linked directly with glutaraldehyde (crosslinking to give CLEAs). Corresponding and other immobilization processes are described, for example, in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim.

The reaction (reduction of butan-2-one to butan-2-ol) may be carried out in aqueous or nonaqueous reaction media or in 2-phase systems or (micro)emulsions. The aqueous reaction media are preferably buffered solutions which usually have a pH of from 4 to 8, preferably from 5 to 8. The aqueous solvent may, in addition to water, also contain at least one alcohol, for example ethanol or isopropanol or dimethyl sulfoxide.

Nonaqueous reaction media mean reaction media which contain less than 1% by weight, preferably less than 0.5% by weight, water, based on the total mass of the reaction medium. The reaction is preferably carried out in an organic solvent.

Examples of suitable solvents are aliphatic hydrocarbons, preferably having from 5 to 8 carbon atoms, such as pentane, cyclopentane, hexane, cyclohexane, heptane, octane or cyclooctane, halogenated aliphatic hydrocarbons, preferably having one or two carbon atoms, such as dichloromethane, chloroform, carbon tetrachloride, dichloroethane or tetrachloroethane, aromatic hydrocarbons such as benzene, toluene, the xylenes, chlorobenzene or dichlorobenzene, aliphatic acyclic and cyclic ethers or alcohols, preferably having from 4 to 8 carbon atoms, such as diethyl ether, methyl tert-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures thereof. Particular preference is given to using the above-mentioned ethers, in particular tetrahydrofuran.

The reduction with ADH is preferably carried out in an aqueous-organic, in particular aqueous, reaction medium.

Butan-2-one is used in the enzymic reduction preferably at a concentration of from 0.1 g/l to 500 g/l, particularly preferably from 1 g/l to 50 g/l, and may subsequently be fed in continuously or batchwise.

The enzymic reduction is usually carried out at a reaction temperature below the deactivation temperature of the dehydrogenase used and above $-10°$ C. Said temperature is particularly preferably in the range from 0 to 100° C., in particular from 15 to 60° C. and especially from 20 to 40° C., for example at about 30° C.

The procedure may involve, for example, initially introducing butan-2-one with the ADH, the solvent and, where appropriate, the coenzymes, where appropriate with a second dehydrogenase for regenerating the coenzyme, and/or further reducing agents and mixing the mixture, for example by stirring or shaking. However, it is also possible to immobilize the dehydrogenase(s) in a reactor, for example in a column and to conduct a mixture containing butan-2-one and, where appropriate, coenzymes and/or cosubstrates through the reactor. To this end, the mixture may be circulated through the reactor, until the desired conversion has been achieved. In the process, the keto group of butan-2-one is reduced to an OH group, producing mainly the (S)-enantiomer of the alcohol. The reduction is usually carried out to a conversion of at least 70%, particularly preferably of at least 85% and in particular of at least 95%, based on the butan-2-one present in the mixture. The progress of the reaction, i.e. the sequential reduction of the ketone, may be monitored here by customary methods such as gas chromatography or high pressure liquid chromatography.

The invention also comprises the use of "functional equivalents" of the specifically disclosed enzymes having butan-2-ol-dehydrogenase activity.

"Functional equivalents" or analogs of the specifically disclosed enzymes are, for the purposes of the present invention, polypeptides which differ therefrom and which furthermore possess the desired biological activity such as, for example, substrate specificity. Thus, for example, "functional equivalents" mean enzymes which reduce from butan-2-one to the corresponding S-alcohol and which have at least 20%, preferably 50%, particularly preferably 75%, very particularly preferably 90%, of the activity of an enzyme comprising any of the amino acid sequences listed under SEQ ID NO:2. Moreover, functional equivalents are preferably stable between pH 4 to 10 and advantageously possess a pH optimum between pH 5 and 8 and a temperature optimum in the range from 20° C. to 80° C.

"Functional equivalents" mean, according to the invention, in particular also mutants which have in at least one sequence position of the abovementioned amino acid sequences an amino acid other than the specifically mentioned one but which nevertheless possess one of the abovementioned biological activities. "Functional equivalents" thus comprise the mutants obtainable by one or more amino acid additions, substitutions, deletions and/or inversions, it being possible for said modifications to occur in any sequence position, as long as they result in a mutant having the property profile of the invention. Functional equivalence in particular also exists, if the reactivity patterns between the mutant and the unmodified polypeptide correspond qualitatively, i.e., for example, the same substrates are reacted at different rates.

Examples of suitable amino acid substitutions can be found in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described and also "functional derivatives".

In this context, "precursors" are natural or synthetic precursors of the polypeptides with or without the desired biological activity.

"Functional derivatives" of polypeptides of the invention may likewise be prepared with the aid of known techniques at functional amino acid side groups or at their N-terminal or C-terminal ends. Derivatives of this kind comprise, for example, aliphatic esters of carboxylic acid groups, amides of carboxylic acid groups, which amides are obtainable by reacting with ammonia or with a primary or secondary amine; N-acyl derivatives of free amino groups, which derivatives are prepared by reacting with acyl groups; or O-acyl derivatives of free hydroxyl groups, which derivatives are prepared by reacting with acyl groups.

In the case of a possible protein glycosylation, "functional equivalents" of the invention include proteins of the above-described type in deglycosylated or glycosylated form and also modified forms which can be obtained by altering the glycosylation pattern.

"Functional equivalents" naturally also include polypeptides which are available from other organisms and also naturally occurring variants. For example, areas of homologous sequence regions can be established by sequence comparison and equivalent enzymes can be determined on the basis of the specific guidelines of the invention.

"Functional equivalents" likewise comprise fragments, preferably individual domains or sequence motifs, of the polypeptides of the invention, which fragments have, for example, the desired biological function.

"Functional equivalents" are moreover fusion proteins which contain any of the above-mentioned polypeptide sequences or functional equivalents derived therefrom and at least one further heterologous sequence which is functionally different therefrom and is functionally linked N-terminally or C-terminally (i.e. without any substantial reciprocal functional impairment of the fusion protein moieties). Nonlimiting examples of such heterologous sequences are signal peptides or enzymes, for example.

Homologs of the proteins of the invention may be identified by screening combinatorial libraries of mutants such as truncation mutants, for example. For example, a variegated library of protein variants may be generated by combinatorial mutagenesis at the nucleic acid level, for example by enzymically ligating a mixture of synthetic oligonucleotides. There are a large number of methods which may be used for preparing libraries of potential homologs from a degenerate oligonucleotide sequence. A degenerate gene sequence may be synthesized chemically in a DNA synthesizer and the synthetic gene may then be ligated into a suitable expression vector. Using a degenerate set of genes makes it possible to prepare all the sequences in a mixture which encode the desired set of potential protein sequences. Processes for synthesizing degenerate oligonucleotides are known to the skilled worker (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

A plurality of techniques for screening gene products of combinatorial libraries which have been prepared by point mutations or truncation and for screening cDNA libraries for gene products having a selected property are known in the prior art. These techniques can be adapted for rapidly screening the gene libraries which have been generated by combinatorial mutagenesis of homologs of the invention. The most frequently employed techniques for screening large gene libraries which are subject to high-throughput analysis comprise cloning the gene library into replicable expression vectors, transforming the appropriate cells with the resulting vector library and expressing the combinatorial genes under conditions under which detection of the desired activity facilitates isolation of the vector which encodes the gene whose product was detected. Recursive ensemble mutagenesis (REM), a technique which increases the frequency of functional mutants in the libraries, may be used in combination with the screening tests in order to identify homologs (Arkin and Yourvan (1992) PNAS 89:7811-7815; Delgrave et al. (1993) Protein Engineering 6(3):327-331).

The invention relates furthermore to nucleic acid sequences (single- and double-stranded DNA and RNA sequences, such as cDNA and mRNA, for example) which code for an enzyme with dehydrogenase activity of the invention. Preference is given to nucleic acid sequences which code, for example, for amino acid sequences according to SEQ ID NO:2 or for characteristic partial sequences thereof, or which comprise nucleic acid sequences according to SEQ ID NO:1 or characteristic partial sequences thereof.

All of the nucleic acid sequences mentioned herein can be prepared in a manner known per se by chemical synthesis from the nucleotide building blocks, for example by means of fragment condensation of individual overlapping, complementary nucleic acid building blocks of the double helix. Oligonucleotides may, for example, be synthesized chemically, in a known manner, using the phosphoamidite method (Voet, Voet, 2nd edition, Wiley Press New York, pages 896-897). The assembly of synthetic oligonucleotides and filling-in of gaps with the aid of the DNA polymerase Klenow fragment and ligation reactions and also general cloning methods are described in Sambrook et al. (1989), Molecular Cloning: A laboratory manual, Cold Spring Harbor Laboratory Press.

The invention also relates to nucleic acid sequences (single- and double-stranded DNA and RNA sequences, such as cDNA and mRNA, for example) which code for any of the above polypeptides and their functional equivalents which are accessible by using artificial nucleotide analogs, for example.

The invention relates both to isolated nucleic acid molecules which code for polypeptides or proteins of the invention or for biologically active sections thereof and to nucleic acid fragments which may be used, for example, for use as hybridization probes or primers for identifying or amplifying coding nucleic acids of the invention.

The nucleic acid molecules of the invention may moreover contain untranslated sequences from the 3' and/or the 5' end of the coding gene region.

The invention furthermore comprises the nucleic acid molecules complementary to the specifically described nucleotide sequences, or a section thereof.

The nucleotide sequences of the invention make it possible to generate probes and primers which can be used for identifying and/or cloning homologous sequences in other cell types and organisms. Probes and primers of this kind usually comprise a nucleotide sequence region which hybridizes, under "stringent" conditions (see below), to at least about 12, preferably at least about 25, such as, for example, about 40, 50 or 75, consecutive nucleotides of a sense strand of a nucleic acid sequence of the invention or of a corresponding antisense strand.

An "isolated" nucleic acid molecule is removed from other nucleic acid molecules which are present in the natural source of the nucleic acid and may moreover be essentially free of other cellular material or culture medium when it is prepared by means of recombinant techniques or free of chemical precursors or other chemicals when it is synthesized chemically.

A nucleic acid molecule of the invention may be isolated by means of standard molecular-biological techniques and the sequence information which is provided according to the invention. For example, cDNA may be isolated from a suitable cDNA library by using one of the specifically disclosed complete sequences or a section thereof as hybridization probe and using standard hybridization techniques (as described, for example, in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). In addition, a nucleic acid molecule comprising any of the disclosed sequences or a section thereof can be isolated by polymerase chain reaction, the oligonucleotide primers which have been constructed on the basis of this sequence being used. The nucleic acid amplified in this way may be cloned into a suitable vector and characterized by DNA sequence analysis. The oligonucleotides of the invention may also be prepared by standard synthesis processes using, for example, an automatic DNA synthesizer.

The nucleic acid sequences of the invention can be identified and isolated in principle from any organisms. Advantageously, the nucleic acid sequences of the invention or the homologs thereof can be isolated from fungi, yeasts, archeae or bacteria. Bacteria which may be mentioned are Gram-negative and Gram-positive bacteria. The nucleic acids of the invention are preferably isolated from Gram-negative bacteria, advantageously from α-proteobacteria, β-proteobacteria or γ-proteobacteria, particularly preferably from bacteria of the orders Acidithiobacillales, Alteromonadales, Chromatiales, Enterobacteriales, Legionellales, Methylococcales, Oceanospirillales, Pasteurellales, Pseudomonadales, Thiotrichales, Vibrionales, Xanthomonadales. Very particularly preferably from bacteria of the family Enterobacteriaceae. Especially preferably from the genus *Escherichia*. Especially preferably from the species *Escherichia albertii, Escherichia blattae, Escherichia coli, Escherichia fergusonii, Escherichia hermannii, Escherichia senegalensis* and *Escherichia vulneris*.

Particular preference is given to using dehydrogenases from *Escherichia coli*.

Nucleic acid sequences of the invention can, for example, be isolated from other organisms by using customary hybridization processes or the PCR technique, for example by way of genomic or cDNA libraries. These DNA sequences hybridize with the sequences of the invention under standard conditions. Use is advantageously made, for the hybridization, of short oligonucleotides of the conserved regions, for example from the active site, which conserved regions may be identified in a manner known to the skilled worker by way of comparisons with a dehydrogenase of the invention. However, it is also possible to use longer fragments of the nucleic acids of the invention or the complete sequences for the hybridization. Said standard conditions vary depending on the nucleic acid employed (oligonucleotide, longer fragment or complete sequence) or depending on which nucleic acid type, DNA or RNA, is used for the hybridization. Thus, for example, the melting temperatures for DNA:DNA hybrids are approx. 10° C. lower than those for DNA:RNA hybrids of the same length.

Depending on the nucleic acid, standard conditions mean, for example, temperatures between 42 and 58° C. in an aqueous buffer solution having a concentration of between 0.1 to 5×SSC (1×SSC=0.15 M NaCl, 15 mM sodium citrate, pH 7.2) or additionally in the presence of 50% formamide, such as, for example, 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids, the hybridization conditions are advantageously 0.1×SSC and temperatures between about 30° C. to 55° C., preferably between about 45° C. to 55° C. The temperatures indicated for the hybridization are melting temperature values which have been calculated by way of example for a nucleic acid having a length of approx. 100 nucleotides and a G+C content of 50% in the absence of formamide. The experimental conditions for the DNA hybridization are described in specialist textbooks of genetics, such as, for example, Sambrook et al., "Molecular Cloning", Cold Spring Harbor Laboratory, 1989, and can be calculated using formulae known to the skilled worker, for example as a function of the length of the nucleic acids, the type of hybrids or the G+C content. The skilled worker can obtain further information with regard to hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The invention also relates to derivatives of the specifically disclosed or derivable nucleic acid sequences.

Thus, further nucleic acid sequences of the invention may be derived from SEQ ID NO:1 and differ therefrom by the addition, substitution, insertion or deletion of single or two or more nucleotides but still code for polypeptides having the desired property profile.

The invention also comprises those nucleic acid sequences which comprise "silent" mutations or have been altered, as compared with a specifically mentioned sequence, according to the codon usage of a specific source organism or host organism, as well as naturally occurring variants thereof, such as splice variants or allele variants, for example.

The invention also relates to sequences obtainable by way of conservative nucleotide substitutions (i.e. the amino acid in question is replaced with an amino acid of the same charge, size, polarity and/or solubility).

The invention also relates to the molecules which are derived from the specifically disclosed nucleic acids by way of sequence polymorphisms. These genetic polymorphisms can exist between individuals within a population as a result of natural variation. These natural variations usually give rise to a variance of from 1 to 5% in the nucleotide sequence of a gene.

Moreover, derivatives mean fusions with promoters, for example. The promoters which are located upstream of the nucleotide sequences indicated may have been altered by one or more nucleotide replacements, insertions, inversions and/or deletions without, however, the functionality and efficacy of the promoters being impaired. Furthermore, the efficacy of said promoters may be increased by altering their sequence or the promoters may be completely replaced with more active promoters, including those from organisms of other species.

Derivatives also mean variants whose nucleotide sequence in the region from −1 to −1000 bases upstream of the start codon or from 0 to 1000 bases downstream of the stop codon has been altered so as to alter, preferably increase, gene expression and/or protein expression.

The invention furthermore comprises nucleic acid sequences which hybridize with coding sequences mentioned above under "stringent conditions". These polynucleotides can be found by screening genomic or cDNA libraries and, if appropriate, amplified therefrom by means of PCR using suitable primers and then isolated using suitable probes, for example. In addition, polynucleotides of the invention may also be synthesized chemically. This property means the ability of a polynucleotide or oligonucleotide to bind to a virtually complementary sequence under stringent conditions while, under these conditions, unspecific bonds between non-complementary partners are not formed. For this purpose, the sequences should be 70-100%, preferably 90-100%, complementary. The property of complementary sequences of being able to bind specifically to one another is utilized, for example, in the Northern or Southern blot technique or for primer binding in PCR or RT-PCR. Oligonucleotides of at least 30 base pairs in length are usually used for this purpose. In the Northern blot technique, for example, stringent conditions mean the use of a washing solution of 50-70° C., preferably 60-65° C., for example 0.1×SSC buffer containing 0.1% SDS (20×SSC: 3M NaCl, 0.3M sodium citrate, pH 7.0), for eluting unspecifically hybridized cDNA probes or oligonucleotides. As mentioned above, the only nucleic acids to remain bound to one another here are those which are highly complementary. The establishment of stringent conditions is known to the skilled worker and is described, for example, in Ausubel et al., Current Protocols in Molecular Biology, John Wiley & Sons, N.Y. (1989), 6.3.1-6.3.6.

Embodiments of Constructs of the Invention

The invention moreover relates to expression constructs comprising, under the genetic control of regulatory nucleic acid sequences, a nucleic acid sequence coding for a polypeptide of the invention; and also to vectors comprising at least one of these expression constructs.

Such constructs of the invention preferably comprise a promoter 5'-upstream of the particular coding sequence and a terminator sequence 3'-downstream and also, if appropriate, further customary regulatory elements which are in each case operatively linked to the coding sequence.

An "operative linkage" means the sequential arrangement of promoter, coding sequence, terminator and, if appropriate, further regulatory elements in such a way that each of the regulatory elements is able to fulfill its function as required in expressing the coding sequence. Examples of operatively linkable sequences are targeting sequences and also enhancers, polyadenylation signals and the like. Other regulatory elements comprise selectable markers, amplification signals, origins of replication and the like. Suitable regulatory sequences are described, for example, in Goeddel, Gene Expression Technology Methods in Enzymology 185, Academic Press, San Diego, Calif. (1990).

A nucleic acid construct of the invention means in particular those in which the gene for a dehydrogenase of the invention has been operatively or functionally linked to one or more regulatory signals for the purpose of regulating, e.g. increasing, expression of the gene.

In addition to these regulatory sequences, the natural regulation of these sequences may still be present upstream of the actual structural genes and, if appropriate, may have been genetically altered in such a way that the natural regulation has been switched off and expression of the genes has been increased. However, the nucleic acid construct may also have a simpler design, i.e. no additional regulatory signals have been inserted upstream of the coding sequence and the natural promoter, together with its regulation, has not been removed. Instead of this, the natural regulatory sequence is mutated in such a way that there is no longer any regulation and expression of the gene is increased.

A preferred nucleic acid construct also advantageously contains one or more of the previously mentioned enhancer sequences which are functionally linked to the promoter and which enable expression of the nucleic acid sequence to be increased. Additional advantageous sequences such as further regulatory elements or terminators may also be inserted at the 3' end of the DNA sequences. The nucleic acids of the invention may be present in the construct in one or more copies. The construct may also contain additional markers such as antibiotic resistances or auxotrophy-complementing genes, if appropriate for the purpose of selecting said construct.

Regulatory sequences which are advantageous for the process of the invention are present, for example, in promoters such as the cos, tac, trp, tet, trp-tet, lpp, lac, lpp-lac, lacI$^q$, T7, T5, T3, gal, trc, ara, rhaP (rhaP$_{BAD}$)SP6, lambda-P$_R$ or lambda-P$_L$ promoter, which promoters are advantageously used in Gram-negative bacteria. Further advantageous regulatory sequences are present, for example, in the Gram-positive promoters amy and SPO2, in the yeast or fungal promoters ADC1, MFalpha, AC, P-60, CYC1, GAPDH, TEF, rp28, ADH. The pyruvate decarboxylase and methanoloxidase promoters, for example from *Hansenula*, are also advantageous in this connection. It is also possible to use artificial promoters for regulation.

For the purpose of expression in a host organism, the nucleic acid construct is advantageously inserted into a vector such as a plasmid or a phage, for example, which enables the genes to be expressed optimally in the host. Vectors mean, in addition to plasmids and phages, also any other vectors known to the skilled worker, i.e., for example, viruses such as SV40, CMV, baculovirus and adenovirus, transposons, IS elements, phasmids, cosmids, and linear or circular DNA. These vectors may be replicated autonomously in the host organism or replicated chromosomally. These vectors constitute a further embodiment of the invention. Examples of suitable plasmids are pLG338, pACYC184, pBR322, pUC18, pUC19, pKC30, pRep4, pHS1, pKK223-3, pDHE19.2, pHS2, pPLc236, pMBL24, pLG200, pUR290, pIN-III[113]-B1, Igt11 or pBdCl, in *E. coli*, pIJ101, pIJ364, pIJ702 or pIJ361, in *Streptomyces*, pUB110, pC194 or pBD214, in *Bacillus*, pSA77 or pAJ667, in *Corynebacterium*, pALS1, pIL2 or pBB116, in fungi, 2alphaM, pAG-1, YEp6, YEp13 or pEMBLYe23, in yeasts, or pLGV23, pGHlac+, pBIN19, pAK2004 or pDH51, in plants. Said plasmids are a small selection of the possible plasmids. Other plasmids are well known to the skilled worker and can be found, for example, in the book Cloning Vectors (Eds. Pouwels P. H. et al. Elsevier, Amsterdam-New York-Oxford, 1985, ISBN 0 444 904018).

For the purpose of expressing the other genes which are present, the nucleic acid construct advantageously also contains 3'-terminal and/or 5'-terminal regulatory sequences for increasing expression, which are selected for optimal expression in dependence on the host organism and the gene or genes selected.

These regulatory sequences are intended to enable the genes and protein expression to be specifically expressed. Depending on the host organism, this may mean, for example, that the gene is expressed or overexpressed only after induction or that it is expressed and/or overexpressed immediately.

In this connection, the regulatory sequences or factors may preferably influence positively and thereby increase expression of the genes which have been introduced. Thus, the regulatory elements may advantageously be enhanced at the level of transcription by using strong transcription signals such as promoters and/or enhancers. However, in addition to this, it is also possible to enhance translation by improving the stability of the mRNA, for example.

In a further embodiment of the vector, the vector which contains the nucleic acid construct of the invention or the nucleic acid of the invention may also advantageously be introduced into the microorganisms in the form of a linear DNA and be integrated into the genome of the host organism by way of heterologous or homologous recombination. This linear DNA may consist of a linearized vector such as a plasmid or only of the nucleic acid construct or the nucleic acid of the invention.

In order to be able to express heterologous genes optimally in organisms, it is advantageous to alter the nucleic acid sequences in accordance with the specific codon usage employed in the organism. The codon usage can readily be determined with the aid of computer analyses of other known genes from the organism in question.

An expression cassette of the invention is prepared by fusing a suitable promoter to a suitable coding nucleotide sequence and to a terminator signal or polyadenylation signal. Common recombination and cloning techniques, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987) are used for this purpose.

In order to achieve expression in a suitable host organism, the recombinant nucleic acid construct or gene construct is advantageously inserted into a host-specific vector which enables the genes to be expressed optimally in the host. Vectors are well known to the skilled worker and may be found, for example, in "Cloning Vectors" (Pouwels P. H. et al., Eds., Elsevier, Amsterdam-N.Y.-Oxford, 1985).

Host Organisms Useful According to the Invention

It is possible to prepare, with the aid of the vectors or constructs of the invention, recombinant microorganisms which are, for example, transformed with at least one vector of the invention and which may be used for producing the polypeptides of the invention. Advantageously, the above-described recombinant constructs of the invention are introduced into a suitable host system and expressed. In this connection, familiar cloning and transfection methods known to the skilled worker, such as, for example, coprecipitation, protoplast fusion, electroporation, retroviral transfection and the like, are preferably used in order to cause said nucleic acids to be expressed in the particular expression system. Suitable systems are described, for example, in Current Protocols in Molecular Biology, F. Ausubel et al., Eds., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

According to the invention, it is also possible to prepare homologously recombined microorganisms. For this purpose, a vector which contains at least one section of a gene of the invention or of a coding sequence in which, if appropriate, at least one amino acid deletion, amino acid addition or amino acid substitution has been introduced in order to modify, for example functionally disrupt, the sequence of the invention (knock out vector), is prepared. The introduced sequence may also be a homolog from a related microorganism or be derived from a mammalian, yeast or insect source, for example. Alternatively, the vector used for homologous recombination may be designed in such a way that the endogenous gene is, in the case of homologous recombination, mutated or otherwise altered but still encodes the functional protein (e.g. the upstream regulatory region may have been altered in such a way that expression of the endogenous protein is thereby altered). The altered section of the gene of the invention is in the homologous recombination vector. The construction of vectors which are suitable for homologous recombination is described, for example, in Thomas, K. R. and Capecchi, M. R. (1987) Cell 51:503.

Recombinant host organisms suitable for the nucleic acid of the invention or the nucleic acid construct are in principle any prokaryotic or eukaryotic organisms. Advantageously, microorganisms such as bacteria, fungi or yeasts are used as host organisms. Gram-positive or Gram-negative bacteria, preferably bacteria of the families Enterobacteriaceae, Pseudomonadaceae, Rhizobiaceae, Streptomycetaceae or Nocardiaceae, particularly preferably bacteria of the genera *Escherichia, Pseudomonas, Streptomyces, Nocardia, Burkholderia, Salmonella, Agrobacterium* or *Rhodococcus*, are advantageously used. Very particular preference is given to the genus and species *Escherichia coli*. In addition, further advantageous bacteria can be found in the group of the alpha-proteobacteria, beta-proteobacteria or gamma-proteobacteria.

In this connection, the host organism or host organisms of the invention contain(s) preferably at least one of the nucleic acid sequences, nucleic acid constructs or vectors which are described in this invention and which encode an enzyme with dehydrogenase activity of the invention.

The organisms used in the process of the invention are, depending on the host organism, grown or cultured in a manner known to the skilled worker. Microorganisms are usually grown in a liquid medium which contains a carbon source, usually in the form of sugars, a nitrogen source, usually in the form of organic nitrogen sources such as yeast extract or salts such as ammonium sulfate, trace elements such as iron salts, manganese salts, magnesium salts and, if appropriate, vitamins, at temperatures of between 0° C. and 100° C., preferably between 10° C. and 60° C., while being gassed with oxygen. In this connection, the pH of the nutrient liquid may or may not be kept at a fixed value, i.e. may or may not be regulated during cultivation. The cultivation may be carried out batchwise, semibatchwise or continuously. Nutrients may be introduced at the beginning of the fermentation or be fed in subsequently in a semicontinuous or continuous manner. The ketone may be added directly to the culture or, advantageously, after cultivation. The enzymes may be isolated from the organisms by using the process described in the examples or be used for the reaction as a crude extract.

Recombinant Preparation of the Polypeptides Used According to the Invention

The invention furthermore relates to processes for recombinantly preparing polypeptides used according to the invention or functional, biologically active fragments thereof, with a polypeptide-producing microorganism being cultured, if appropriate expression of the polypeptides being induced and said polypeptides being isolated from the culture. The polypeptides may also be produced in this way on an industrial scale if this is desired.

The recombinant microorganism may be cultured and fermented by known methods. Bacteria may, for example, be propagated in TB medium or LB medium and at a temperature of from 20 to 40° C. and a pH of from 6 to 9. Suitable culturing conditions are described in detail, for example, in T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not secreted into the culture medium, the cells are then disrupted and the product is obtained from the lysate by known protein isolation processes. The cells may be disrupted, as desired, by means of high-frequency ultrasound, by means of high pressure, such as, for example, in a French pressure cell, by means of osmolysis, by the action of detergents, lytic enzymes or organic solvents, by using homogenizers or by a combination of two or more of the processes listed.

The polypeptides may be purified using known chromatographic methods such as molecular sieve chromatography (gel filtration), for example Q Sepharose chromatography, ion exchange chromatography and hydrophobic chromatography, and also using other customary methods such as ultrafiltration, crystallization, salting-out, dialysis and native gel electrophoresis. Suitable processes are described, for example, in Cooper, F. G., Biochemische Arbeitsmethoden, Verlag Walter de Gruyter, Berlin, N.Y. or in Scopes, R., Protein Purification, Springer Verlag, New York, Heidelberg, Berlin.

It may be advantageous to isolate the recombinant protein by using vector systems or oligonucleotides which extend the cDNA by particular nucleotide sequences and thereby code for altered polypeptides or fusion proteins which are used, for example, to simplify purification. Examples of suitable modifications of this kind are "tags" acting as anchors, such as the modification known as the hexa-histidine anchor, or epitopes which can be recognized as antigens by antibodies (described, for example, in Harlow, E. and Lane, D., 1988, Antibodies: A Laboratory Manual. Cold Spring Harbor (N.Y.) Press). These anchors may be used for attaching the proteins to a solid support such as a polymer matrix, for example, which may, for example, be packed into a chromatography column, or may be used on a microtiter plate or on another support.

At the same time, these anchors may also be used for identifying the proteins. The proteins may also be identified by using customary markers such as fluorescent dyes, enzyme markers which, after reaction with a substrate, form a detectable reaction product, or radioactive markers, either on their own or in combination with the anchors, for derivatizing said proteins.

Further Embodiments for Carrying Out the Enzymic Reduction Process of the Invention The dehydrogenases may be used as free or immobilized enzyme in the process of the invention.

The process of the invention is advantageously carried out at a temperature between 0° C. to 95° C., preferably between 10° C. to 85° C., particularly preferably between 15° C. to 75° C.

In the process of the invention, the pH is advantageously kept between pH 4 and 12, preferably between pH 4.5 and 9, particularly preferably between pH 5 and 8.

In the process of the invention, enantiomerically pure or chiral products such as butan-2-ol mean enantiomers which exhibit enantiomer enrichment. Enantiomeric purities of at least 70% ee, preferably of at least 80% ee, particularly preferably of at least 90% ee, very particularly preferably of at least 98% ee, are preferably achieved in the process.

It is possible to use for the process of the invention growing cells which contain the nucleic acids, nucleic acid constructs or vectors of the invention. It is also possible to use resting or disrupted cells. Disrupted cells mean, for example, cells which have been made permeable by way of treatment with solvents, for example, or cells which have been broken up by way of treatment with enzymes, by way of mechanical treatment (e.g. French press or ultrasonication) or by way of another method. The crude extracts obtained in this manner are advantageously suitable for the process of the invention. It is also possible to use purified or partially purified enzymes for the process. Immobilized microorganisms or enzymes which may advantageously be applied in the reaction are likewise suitable.

The process of the invention can be operated batchwise, semi-batchwise or continuously.

The process may advantageously be carried out in bioreactors as described, for example, in Biotechnology, volume 3, 2nd edition, Rehm et al. Eds., (1993), in particular chapter II.

The examples below are intended to illustrate but not to limit the invention. In this context, reference is made to the accompanying figures in which:

depicts a typical reaction profile of a synthesis of (S)-butan-2-ol by way of reduction with a dehydrogenase from *Escherichia coli*.

EXPERIMENTAL SECTION

Example 1

Cloning of the *Escherichia coli* Propanol Dehydrogenase

The sequence of the gene of *Escherichia coli* propanol dehydrogenase has been deposited in databases (GenBank ID 48994873 region: complement (1550852 to 1551892)). Oligonucleotides which were used for amplifying the gene from *Escherichia coli* genomic DNA according to known processes were derived from the nucleic acid sequence of the propanol dehydrogenase gene. The sequence obtained corresponds to the published sequence. The DNA sequence of the oligonucleotides is depicted in table 1.

TABLE 2

Oligonucleotides for preparing the synthetic gene of Escherichia coli propanol dehydrogenase

| | (SEQ ID NO: 3) |
|---|---|
| #1 | GGGAATTCATATGCAGAACATCATCCGAAAAG |
| | (SEQ ID NO: 4) |
| #2 | CCCAAGCTTAGTGACGGAAATCAATC |

PCR conditions:

| 2 µl | 10*Pfu-Ultra buffer (Stratagene ®) |
|---|---|
| 100 ng | primer #1 (cf. Table 1) |
| 100 ng | primer #2 (cf. Table 1) |
| 1 µl | dNTP (10 mM each) |
| approx. 30 ng | *Escherichia coli* chromosomal DNA |
| 1 U | Pfu-Ultra DNA polymerase |
| ad 20 µl | H₂O |

Temperature program:

5 min, 95° C.,
45 sec, 40° C.,
1.5 min, 72° C.,     } (30 cycles)
45 sec, 95° C.,
10 min, 72° C.,
∞, 10° C.

The PCR product (approx. 1050 bp) was digested with the restriction endonucleases NdeI and HindIII and cloned into the pDHE19.2 vector which had been cleaved accordingly (the cloning was carried out as described in DE 19848129). The ligation mixtures were transformed into *E. coli* XL1 Blue (Stratagene®).

The plasmid obtained, pDHE-PDH-L, was transformed into the *E. coli* strain TG10 pA-gro4 pHSG575 (TG10: an RhaA⁻ derivative of *E. coli* TG1 (Stratagene®)); pAgro4: Takeshia, S; Sato, M; Toba, M; Masahashi, W; Hashimoto-Gotoh, T (1987) Gene 61, 63-74; pHSG575: T. Tomoyasu et al (2001), Mol. Microbiol. 40(2), 397-413). The recombinant *E. coli* clone obtained was referred to as *E. coli* LU12418.

Example 2

Provision of Recombinant Propanol Dehydrogenase

*E. coli* LU12418 were grown in 20 ml of LB-Amp/Spec/Cm (100 µg/l ampicillin; 100 µg/l spectinomycin; 20 µg/l chloramphenicol), 0.1 mM IPTG, 0.5 g/l rhamnose in 100 ml Erlenmeyer flasks (baffles) at 37° C. for 18 h, centrifuged at 5000*g/10 min, washed once with 10 mM TRIS*HCl, pH 7.0 and resuspended in 2 ml of the same buffer.

Cell-free protein crude extract was prepared by disrupting *E. coli* LU12418 cell paste 0.7 ml of glass beads (d=0.5 mm) in a vibratory mill (3×5 min, with intermediate cooling on ice).

Example 3

Determination of the Activity of the *E. coli* LU12418 Recombinant Dehydrogenase In each case 6 transformants were grown in 20 ml of LBAmp/Spec/Cm (100 µg/l Amp; 100 mg/l Spec; 20 µg/l Cm), 0.1 mM IPTG, 0.5 g/l rhamnose in 100 ml Erlenmeyer flasks (baffles) at 37° C. for 18 h, centrifuged at 5000*g/10 min, washed once with 10 mM TRIS/HCl, pH 7.0 and resuspended in 2 ml of the same buffer. Cell-free crude extract of *E. coli* LU12418 was obtained by disrupting cells with 0.7 ml of glass beads (d=0.5 mm) in a vibratory mill (3×5 min, with intermediate cooling on ice).

The consumption of reduced cosubstrates during the reduction of ketones can be monitored in a photometer at 340 nm. 10 µl of diluted cell-free crude extract (≅10 µg of protein), 10 µmol of n-propanal and 250 nmol of NADH or NADPH were incubated in 1 ml of 50 mM $KP_i$, 1 mM $MgCl_2$, pH 6.5 at 30° C. 1 unit (1 U) corresponds to the amount of enzyme which reduces 1 µmol of n-propanal in 1 min.

Example 4

Analysis of butan-2-ol

The concentrations of butan-2-one and butan-2-ol can be determined by means of GC. It is also possible, depending on the choice of stationary and mobile phases, to determine the ee value in addition to the concentration.

a) Achiral Analysis

The reaction was quantified using the following system:

| Stationary phase: | Chromoltih SpeedROD RP18, 50*4, 6 µm, Merck (Darmstadt, Germany), heated to 45° C. |
|---|---|
| Mobile phase: | eluent A: 10 mM $KH_2PO_4$, pH 2.5 |
| | eluent B: acetonitrile |
| | gradient: 0-0.5 min, 35% B; 0.5-1.0 min 35 to 80% B; 1.0-1.2 min 80% B; 1.2-1.3 min 80%-35% B; 1.3-2.0 min 35% B; |
| Flow rate: | 1.5 ml/min |
| Detection: | UV detection at 230 and 260 nm |
| Retention times: | butan-2-one: approx. 1.6 min |
| | butan-2-ol: approx. 1.3 min |

Using authentic material, a calibration series is produced, on the basis of which the concentration of unknown samples can be determined.

| b) chiral analysis | |
|---|---|
| Stationary phase: | Chiracel OD-H, 250*4, 6 µm, Daicel, heated to 40° C. |
| Mobile phase: | eluent A: n-hexane |
| | eluent B: iso-propanol |
| | isocratic with 2.5% B |
| Flow rate: | 1.0 ml/min |
| Detection: | UV detection at 230 and 260 nm |
| Retention times: | butan-2-one: approx. 9.5 min |
| | (1S)-butan-2-ol: approx. 16.6 min |
| | (1R)-butan-2-ol: approx. 18.3 min |

Using authentic material, a calibration series is produced, on the basis of which the concentration of unknown samples can be determined.

Example 5

Provision of Glucose Dehydrogenase for Cofactor Regeneration and Cofactor Regeneration with Glucose Dehydrogenase (Enzyme Coupling)

Glucose dehydrogenase may be used for cofactor regeneration. The enzyme is commercially available (e.g. Jülich Fine Chemicals, Order No. 22.10 or 19.10). Below, the gene of *Bacillus subtilis* glucose dehydrogenase (GenBank Acc. No. M12276) was used and cloned in the pUC19 plasmid in an *E. coli* XL10 Gold clone. This construct is referred to as *E. coli* LU11293.

The following medium was prepared for fermentation of *E. coli* LU11293:

| | |
|---|---|
| 560 g | yeast extract (65%) |
| 448 g | tryptone (Difco) |
| 42 g | $KH_2PO_4$ |
| 84 g | $Na_2HPO_4$ |
| 644 g | glycerol (99%) |
| 100 ml | SL4 solution (5×) |
| 1 g | Tegosipon 3062 |
| | Dilute medium with water to 13.5 l, adjust pH to 7.0, remove approx. 300 ml for preculture, then sterilize at 122° C. for 30 min. |
| | Add sterile salt solution* (remove the salt solution for the shaker flasks beforehand, see protocol). |

*Salt solution:
2.1 g $CaCl_2 * 2 H_2O$
3.5 g $MgSO_4 * 7 H_2O$
14 g $NH_4Cl$
14 ml ampicillin solution (100 mg/ml)
dissolve in 500 ml of water and sterilize by filtration In each case 150 ml of medium were sterilized in two 1 l Erlenmeyer flasks and completed with 5 ml of sterile salt solution. After inoculating from an LB ampicillin agar plate, the precultures were incubated at 37° C. and 200 rpm for 12 hours and added to the fermentation medium. The fermentation was started at 37° C., 0.1 bar of internal pressure, pH 7.0 (regulation with 20% phosphoric acid and 25% NaOH), with a gassing rate of 7.5 l/min and 300 rpm (regulation of $pO_2$ between 20 and 50% with 10-20 l/min inlet air and 500-1500 rpm). After 2 h, 0.1 mM IPTG was added for induction and the fermentation was stopped after a total time of 13 h. After harvesting and washing the cells (1.3 kg), the latter were stored at −20° C. until use (2-20 g/l in the reaction mixture).

Equimolar amounts of glucose and butan-2-one were admixed with 1-30 U/ml glucose dehydrogenase crude extract and 1-30 U/ml propanol dehydrogenase crude extract. 0.02-1 mmol/l NAD or NADP or 0.02-1 mmol/l NADH or NADPH were dissolved in buffer and incubated at 10-60° C. The pH was maintained at a constant level by automatic addition of base.

Example 6

Cofactor Regeneration with Propanol Dehydrogenase (Substrate Coupling)

The cofactor may also be regenerated by the propanol dehydrogenase itself. In this case, addition of a separate regeneration enzyme is not required. The propanol dehydrogenase accepts various monohydric alcohols as reducing agents. They are oxidized to the corresponding carbonyl compounds. A monohydric alcohol which is suitable for regenerating NADH or NADPH with propanol dehydrogenase is iso-propanol.

Example 7

Cofactor Regeneration with Formate Dehydrogenase (Enzyme Coupling)

Formate dehydrogenase may be used for cofactor regeneration. The enzyme can be obtained from commercial (e.g. Jülich Fine Chemicals Order No. 09.11, 24.11 or 25.10). Similarly to Example 5, the cofactors may thus also be regenerated with formate dehydrogenase. This involves using equimolar amounts of formate and butan-2-one with 1-30 U/ml formate dehydrogenase crude extract and 1-30 U/ml propanol dehydrogenase crude extract. 0.02-1 mmol/l NAD or NADP or 0.02-1 mmol/l NADH or NADPH were dissolved in buffer and incubated at 10-60° C. The pH was maintained at a constant level by automatic addition of acid.

Example 8

Preparation of (S)-butan-2-ol Using the Recombinant Propanol Dehydrogenase of *Escherichia coli*

*E. coli* LU12418 were cultivated, harvested and disrupted according to example 2.

Figure 1:
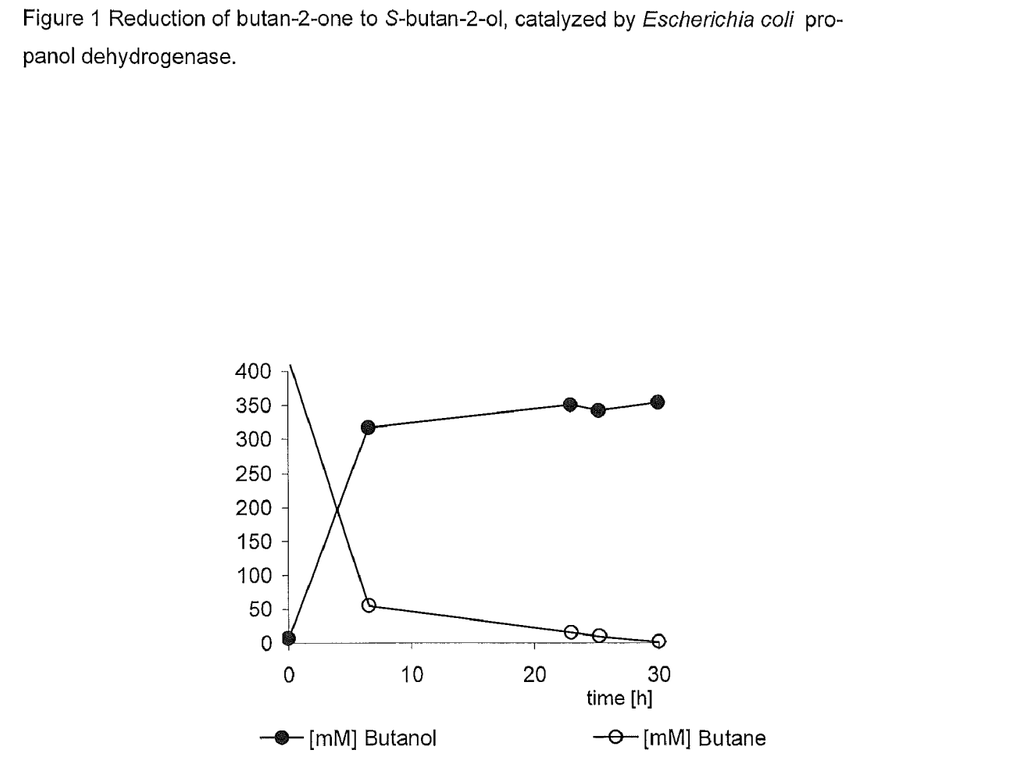

270 g (1.5 mol) of D-glucose, 135 ml (1.5 mol) of butan-2-one, 63 ml of GDH crude extract (≅30.5 kU), 95 ml of PDH crude extract (≅20 kU) and 400 mg (0.6 mmol) of NAD or NADP or of NADH or NADPH were dissolved in $KP_i$ buffer (50 mM $KP_i$, 1 mM $MgCl_2$, pH 6.5) and incubated at 30° C. The reaction mixture had a starting volume of three liters. The pH was maintained at a constant level by automatic addition of 2M NaOH. FIG. 1 depicts a typical reaction profile.

What is claimed is:

1. A process for preparing (S)-butan-2-ol, wherein the process comprises reducing butan-2-one in the presence of an alcohol dehydrogenase comprising:
   (i) the polypeptide sequence of SEQ ID NO: 2, or
   (ii) a polypeptide sequence which is at least 95% identical to the sequence of SEQ ID NO: 2, wherein the reduction is carried out using NADH or NADPH as a cofactor.

2. The process according to claim 1, wherein the reduction is carried out in the presence of a cofactor that is regenerated enzymatically.

3. The process according to claim 1, wherein the reduction is carried out in the presence of a cofactor that is regenerated by glucose dehydrogenase.

4. The process according to claim 1, wherein the reduction is carried out in an aqueous system.

5. The process according to claim 1, wherein the alcohol dehydrogenase is present in an immobilized form.

6. The process according to claim 1, wherein the alcohol dehydrogenase used is expressed in *E. coli*.

7. The process according to claim 1, wherein the alcohol dehydrogenase is encoded by the nucleic acid sequence of SEQ ID NO: 1.

* * * * *